United States Patent [19]
Freed et al.

[11] 3,966,815
[45] June 29, 1976

[54] PREPARATION OF 5,8-METHANO-5H-BENZOCYCLOHEPTEN-10-AMINES

[75] Inventors: Meier E. Freed, Paoli; John R. Potoski, Spring City, both of Pa.

[73] Assignee: American Home Products Corporation, New York, N.Y.

[22] Filed: May 31, 1974

[21] Appl. No.: 475,223

[52] U.S. Cl. .................... 260/570.8 R; 260/327 M; 260/327 TH; 260/340.9; 260/456 R; 260/566 R; 260/590 B; 260/512 C; 424/311; 424/330

[51] Int. Cl.² ........................................ C07C 87/29

[58] Field of Search .......... 260/571, 570.9, 570.8 R

[56] References Cited
OTHER PUBLICATIONS
Index Chemicus, 34, 116524, (1969).

Primary Examiner—D. Horwitz
Attorney, Agent, or Firm—Robert Wiser

[57] ABSTRACT

Processes for the preparation of 5,8-methano-5H-benzocyclohepten-10-amines are disclosed. The final products are analgesics.

12 Claims, 1 Drawing Figure

PREPARATION OF 5,8-METHANO-5H-BENZOCYCLOHEPTEN-10-AMINES

BACKGROUND OF THE INVENTION

A method for the preparation of 5,8-methano-5H-benzocyclohepten-10-amines is given in our copending application Ser. No. 262,849, filed June 14, 1972, now U.S. Pat. No. 3,836,670, and Belgian Patent No. 776,173. The present invention provides an alternative synthesis of these compounds.

SUMMARY OF THE INVENTION

The invention sought to be patented in its first process aspect resides in the concept of a process for the preparation of:

compounds of the formula:

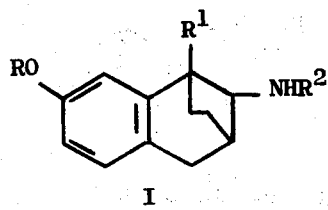

I wherein R is lower alkyl, or phen(lower)alkyl; $R^1$ is lower alkyl; and $R^2$ is hydrogen, lower alkyl, or phen(lower)alkyl; which comprises:

a. treating a compound of the formula:

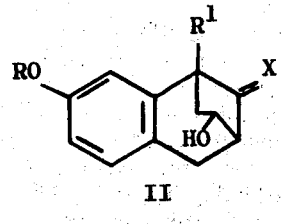

II wherein R is lower alkyl, or phen(lower)alkyl; $R^1$ is lower alkyl; and X is a ketone protecting group which is stable in the presence of a base; with a compound of the formula:

A—SO₂—Y wherein A is halo; and Y is straight or branched chain alkyl of from 1 to 10 carbon atoms, or cyclo alkyl of from 1 to 10 carbon atoms, or carbocyclic aryl to produce a compound of the formula:

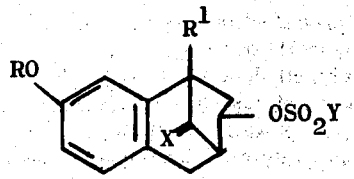

wherein R, $R^1$, X, and Y are as defined hereinabove;

b. treating the product of step (a) above with base in the presence of an inert solvent and heat to produce a compound of the formula:

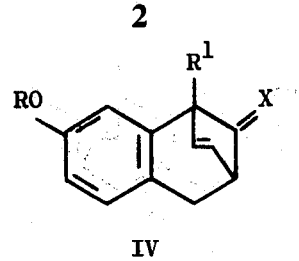

IV wherein R, $R^1$, and X are as defined hereinabove;

c. removing the protecting group from the ketone function of the product of step (b) to produce a compound of the formula:

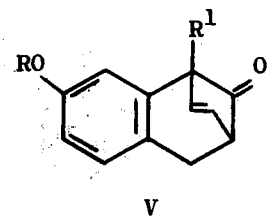

V wherein R and $R^1$ are as defined hereinabove;

d. treating the product of step (c) above with a compound of the formula:

H₂N—Z wherein Z is hydrogen, hydroxyl, lower alkyl, lower alkenyl, lower alkynyl, or phen(lower)alkyl; to form a compound of the formula:

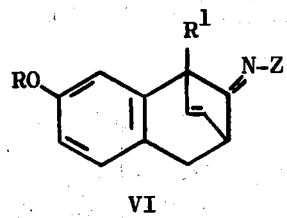

VI wherein R, $R^1$, and Z are as defined hereinabove; and e. reducing the imino function and non-aromatic unsaturation of the product of step (d) above.

The tangible embodiments produced by the first process aspect of the invention possess the inherent general physical properties in the acid salt form of being high melting white crystalline solids, substantially soluble in water and polar organic solvents such as lower aliphatic alcohols and the like.

Examination of the products produced by the aforedescribed process reveals, upon infrared, nuclear magnetic resonance, mass spectral and thin layer chromatographic analysis, spectral data and migration rates, supporting the molecular structure hereinbefore set forth. The tangible embodiments produced by the first process aspect of the invention possess the inherent applied use characteristics of exerting analgesic effects in warm-blooded animals.

The invention sought to be patented in its second process aspect resides in the concept of a process for the production of compounds of the formula:

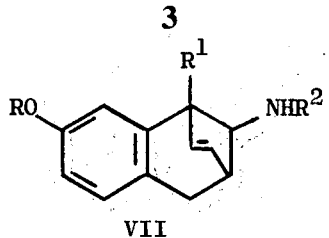

VII wherein R is lower alkyl, or phen(lower)alkyl; R² is hydrogen, lower alkyl, lower alkenyl, lower alkynyl or phen(lower)alkyl; and R¹ is lower alkyl; which comprises:

a. treating a compound of the formula:

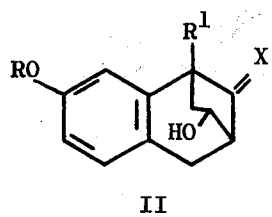

II wherein R and R¹ are as defined hereinabove; and X is a ketone protecting group which is stable in the presence of base; with a compound of the formula:

A—SO₂—Y wherein A is halo; and Y is straight or branched chain alkyl of from 1 to 10 carbon atoms, or cyclo alkyl of from 1 to 10 carbon atoms, or carbocyclic aryl; to produce a compound of the formula:

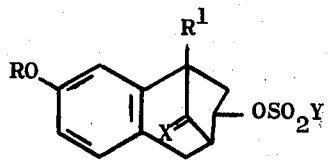

wherein R, R¹, X, and Y are as defined hereinabove;

b. treating the product of step (a) above with base in the presence of an inert solvent and heat to produce a compound of the formula:

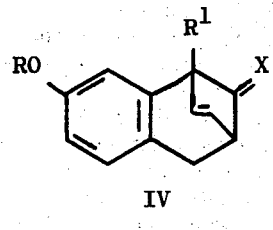

IV wherein R, R¹, and X is as defined hereinabove;

c. removing the protecting group from the ketone function of the product of step (b) to produce a compound of the formula:

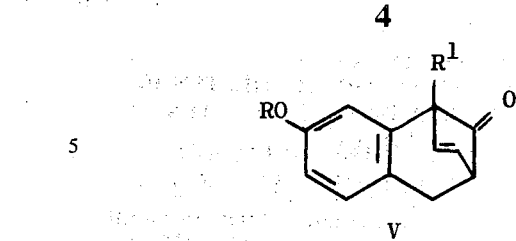

V wherein R and R¹ are as defined hereinabove;

d. treating the product of step (c) above with a compound of the formula:

H₂N—Z wherein Z is hydrogen, hydroxyl, lower alkyl, lower alkenyl, lower alkynyl, or phen(lower)alkyl; to form a compound of the formula:

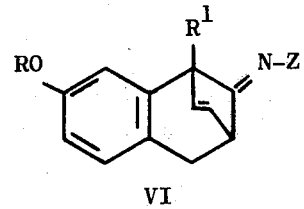

VI wherein R, R³, and Z are as defined hereinabove; and e. reducing the imino function of the product of step (d) above.

The tangible embodiments produced by the second process aspect of the invention possess the inherent general physical properties of being, in the acid salt form, crystalline solids, substantially soluble in water and polar organic solvents such as lower aliphatic alcohols and the like.

Examination of the products produced by the aforesiad process reveals, upon infrared, nuclear magnetic resonance, mass spectral, and gas chromatographic examination, spectral data, and elution rates supporting the molecular structure hereinbefore set forth.

The tangible embodiments produced by the second process aspect of the invention possess the inherent applied use characteristic of being intermediates in the synthesis of compounds of Formula I.

DESCRIPTION OF THE PREFERRED EMBODIMENTS

Figure 1:
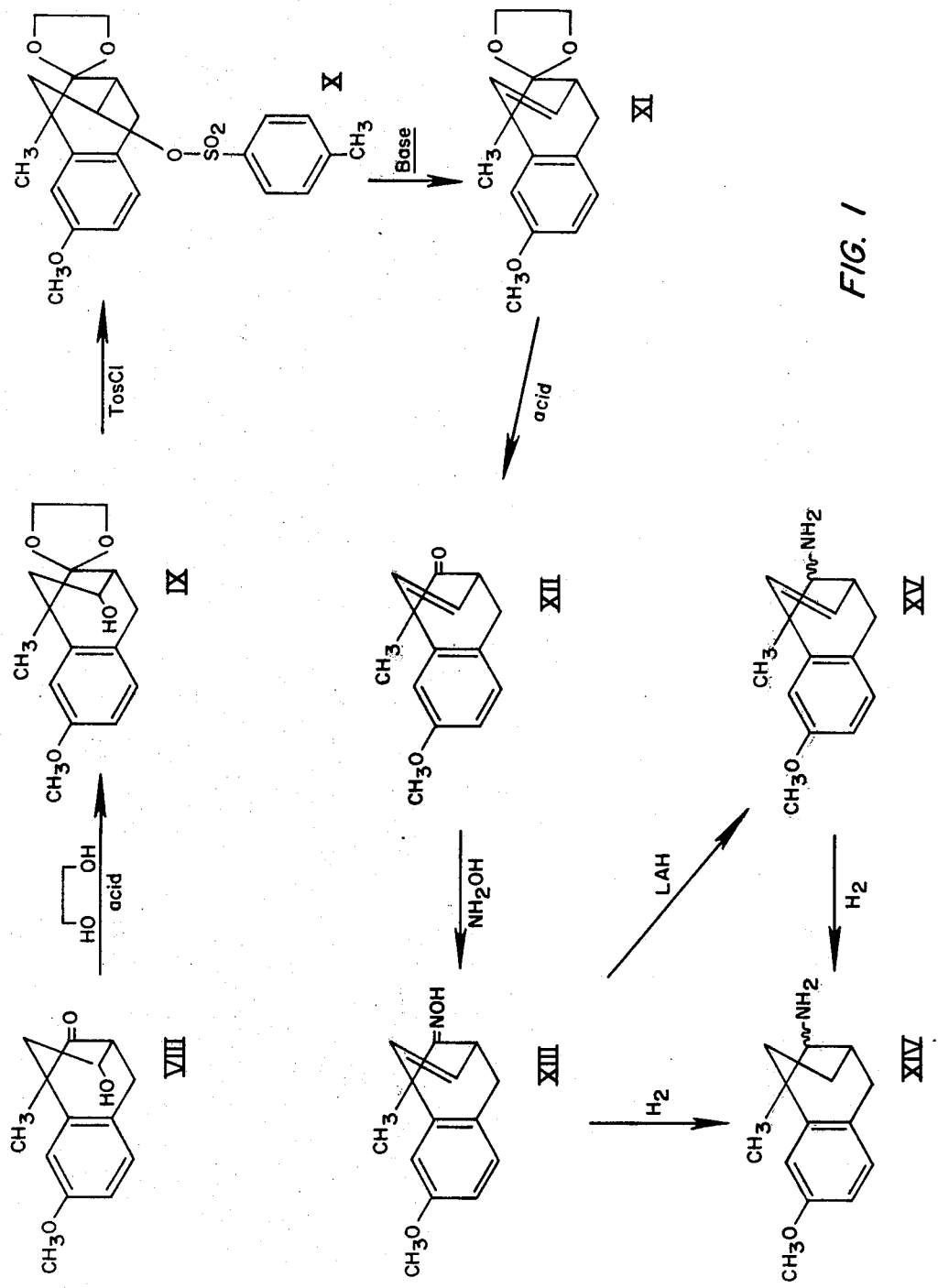

In describing the processes of the invention, reference will be made to the FIGURE, wherein are illustrated schematically, processes for the preparation of a specific embodiment of Formula I, namely 6,7,8,9-tetrahydro-3-methoxy-5-methyl-5,8-methano-5H-benzocyclohepten-10-amine (XIV) and of a specific embodiment of Formula VII, namely 8,9-dihydro-3-methoxy-5-methyl-5,8-methano-5H-benzocyclohepten-10-amine(XV).

6,7,8,9-Tetrahydro-7-hydroxy-3-methoxy-5-methyl-5,8-methano-5H-benzocyclononen-10-one (VIII) is treated with ethylene glycol, in the presence of a catalytic amount of acid, in an inert solvent, conveniently benzene, at elevated temperature, conveniently the reflux temperature of the solvent employed, while removing water during the course of the reaction, to give 6,7,8,9-tetrahydro-7-hydroxy-3-methoxy-5-methyl-5,8-methano-5H-benzocyclononen-10-one, 10-ethylene ketal (IX). If desired, IX may be isolated by standard techniques. Chromatography on silica gel is a convenient method. Treatment of IX with p-toluene sulfonyl chloride in the presence of a solvent and a hydrogen chloride scavenger, conveniently excess pyridine, at reduced temperature, conveniently 0° to 10°C. gives 6,7,8,9-tetrahydro-3-methoxy-5-methyl-7-p-toluensulfonyloxy-5,8-methano-5H-benzocyclohepten-10-one, 10-ethylene ketal (X). Isolation of X may, if desired, be accomplished by standard means. Chromatography on silica gel is a convenient method. Treatment of X with strong base, conveniently potassium-t-butoxide in a solvent, conveniently dimethyl sulfoxide at moderately elevated temperature, conveniently 60° to 65° C., gives 8,9-dihydro-3-methoxy-5-methyl-5,8-methano-5H-benzocyclononen-10-one, 10-ethylene ketal (XI). If desired, XI may be isolated by standard means. Chromatography on silica gel is a convenient method. Treatment of XI with aqueous acid, conveniently a 6:5 mixture of acetic acid and water, at elevated temperature, conveniently the reflux temperature of the acid-water system employed gives 8,9-dihydro-3-methoxy-5-methyl-5,8-methano-5H-benzocyclohepten-10-one (XII). Isolation of XII may, if desired, be accomplished by standard means. Concentration of the hydrolysis reaction to about 1/5 volume and dilution with an excess of cold water, followed by removal of the product which separates, and recrystallization from ethanol-water is a convenient method. Treatment of XII with hydroxylamine, conveniently in the form of hydroxylaminehydrochloride in aqueous ethanol in the presence of sodium acetate, at elevated temperature, conveniently the reflux temperature of the system, gives 8,9-dihydro-3-methoxy-5-methyl-5,8-methano-5H-benzocyclohepten-10-one, oxime (XIII). Isolation of XIII may, if desired, be accomplished by standard means. Concentration of the reaction mixture followed by dilution with water and ether, with separation of the organic phase after partition, washing of the organic phase, drying and concentration followed by recrystallization, of the crude product so found, from isopropanol-water is a convenient method. Treatment of XIII with hydrogen at moderate pressure, conveniently 45 psi in the presence of a hydrogenation catalyst, conveniently Raney nickel, and ammonia gives 6,7,8,9-tetrahydro-3-methoxy-5-methyl-5,8-methano-5H-benzocyclohepten-10-amine (XIV). If desired, XIV may be isolated by standard means. Distillation of the free base, and conversion to the crystalline hydrochloride salt is a convenient method. If desired, the $\alpha$ and $\beta$ amino epimers of XIV may also be separated by standard means. Recrystallization of the hydrochloride salt is a convenient method. Treatment of XIII with a hydride reducing agent, such as lithium aluminumhydride, or in a Bouveault Blanc type reduction, for example, dissolving sodium in ethanol, gives 8,9-dihydro-3-methoxy-5$\alpha$-methyl-5,8-methano-5H-benzocyclohepten-10-amine (XV). If desired, XV may be isolated by conventional means. Distillation of the free base and conversion to the hydrochloride salt is a convenient method. If desired, the $\alpha$ and $\beta$ amine epimers of XV may be separated. Recrystallization of the hydrochloride salt is a convenient method. Treatment of XV with hydrogen, at moderate pressure, conveniently platinum oxide, gives XIV. The starting materials for the practice of the invention, namely 6,7,8,9-tetrahydro-3-lower alkoxy, or -phen(lower)alkyloxy-5-lower alkyl-7-hydroxy-5,8-methano-5H-benzocyclohepten-10-ones may be prepared by the method described by Wiesner, Chan, and Demerson in Tetrahedron Letters, page 2893, 1965.

In addition to the ethylene ketal illustrated it will be well within the skill of the journeyman organic chemist to select other suitable ketone protecting groups known in the art to be stable to base, for example, dithioketals, hemithioketals, and semicarbazides. It will similarly be obvious that in place of hydroxyl amine any of the other compounds of the formula $H_2N-Z$ contemplated as within the scope of the invention may be substituted using standard reaction means.

The skilled organic chemist will realize that, when it is desired to simultaneously reduce the imino and non-aromatic unsaturation in a single reaction sequence, catalytic hydrogenation is especially convenient, and that any catalysts known in the art to be useful in reducing imino functions and carbon-carbon double bonds, such as, Raney nickel in the presence of ammonia, Platinum oxide, Palladium on charcoal and the like are convenient for use in the process.

The skilled organic chemist will realize that, when it is desired to reduce the imino function without concomitant reduction of the non-aromatic unsaturation, such reducing agents as the hydride reducing agents, for example lithium aluminum hydride, or a Bouveault-Blanc type reagent, for example, sodium dissolving in an alkanol, are especially convenient.

When compounds of Formula VII are used as intermediates in the production of compounds of Formula I, catalytic reduction of the non-aromatic unsaturation, similar to that described for the conversion of XV to XIV, is a convenient method for accomplishing the transformation.

The methods of removal of the various ketone protecting groups contemplated as part of the invention will similarly be within the skill of the average organic chemist. Typically an acid cleavage will be convenient method, although other methods known in the art for the cleavage of particular protecting groups will also be suitable.

The use of standard means to produce other secondary and tertiary amine derivatives and free phenolic derivatives from compounds of Formula I is described in our Belgian Patent and copending application for Benzobicycloalkane Amines referenced hereinabove. The application of these methods to compounds of Formula Vii will be obvious to one skilled in organic chemistry.

The analgesic activity of the compounds of Formula I is also described in our Belgian Patent and copending application for Benzobicycloalkane Amines referenced hereinabove.

As used herein (except in the definition of Y) the term "lower alkyl" means a saturated hydrocarbon radical, including the straight and branched radicals having from 1 to 4 carbon atoms, among which are, for the purposes of illustration, but without limiting the generality of the foregoing, methyl, ethyl, n-propyl, n-butyl, and i-butyl. The term "lower alkenyl" means an unsaturated hydrocarbon radical including straight and branched radicals, having from 3 to 5 carbon atoms, among which are, for the purposes of illustration, but without limiting the generality of the foregoing, allyl, 2-butenyl, 3-methyl-2-butenyl, 2-methyl-2-butenyl, and 2-pentenyl.

The term "lower alkynyl" means an unsaturated hydrocarbon radical, containing a triple bond, including straight and branched radicals, having from 3 to 6 carbon atoms, among which are, for the purposes of illustration, but without limiting the generality of the foregoing, 2-propynyl, 2-butynyl, 1-butyn-3-yl, and 3-methyl-1-butyn-4-yl. The term "phen(lower)alkyl" means a lower alkyl radical as defined hereinabove substituted in a terminal position by phenyl or phenyl radical substituted by lower alkyl or lower alkyloxy, among which are, for the purposes of illustration, but without limiting the generality of the foregoing, benzyl, phenethyl, o-, m-, or p-anisyl, p- or m-cumenyl, veratryl, 0-, m-, or p-xylyl.

The term "carbocyclic aryl" means an aryl moiety of from 6 to 10 carbon atoms containing 1 or 2 carbocyclic aromatic rings, which may be unsubstituted or contain one or more substituents selected from among the group consisting of lower alkyl, halo(lower)alkyl, halo, and lower alkoxy, among which are, for the purposes of illustration, but without limiting the generality of the foregoing, phenyl, naphthyl, tolyl, methoxy phenyl, and chlorophenyl, and trifluoromethylphenyl.

The following examples further illustrate the best mode contemplated by the inventors for the practice of the invention.

EXAMPLE 1

6,7,8,9-Tetrahydro-7-Hydroxy-3-Methoxy-5-Methyl-5,8-Methano-5H-Benzocyclohepten-10-One,10-Ethylene Ketal 6,7,8,9-Tetrahydro-7-hydroxy-3-methoxy-5-methyl-5,8-methano-5H-benzocyclohepten-10-one (22 g.), p-toluenesulfonic acid (0.5 g.), and ethylene glycol (15 ml.) in benzene (250 ml.) are heated at reflux with azeotropic removal of water. When the reaction is complete, the mixture is cooled, washed with dilute aqueous sodium carbonate, dried over magnesium sulfate, and concentrated to give a product (24 g.).

Infrared Analysis: $\lambda_{max}^{film}$ 3.0 (OH) $\mu$; no absorption at 5.70 (<C=O) $\mu$.

EXAMPLE 2

6,7,8,9-Tetrahydro-3-Methoxy-5-Methyl-7-p-Toluenesulfonyloxy-5,8-Methano-5H-Benzocyclohepten-10-One, 10-Ethylene Ketal To a solution of 6,7,8,9-tetrahydro-7-hydroxy-3-methoxy-5-methyl-5,8-methano-5H-benzocyclohepten-10-one, 10-ethylene ketal (105 g.) in pyridine, which has been cooled to 0° C., is added p-toluenesulfonyl chloride (80 g.). After standing overnight at −10° C. the reaction is diluted with water, and partitioned with diethyl ether. The organic phase is washed with dilute aqueous acid, dried over magnesium sulfate and concentrated to give a glassy product (132 g.).

I. R. Analysis: $\lambda_{max}$ 7.4, 8.6 (sulfonyl ester) $\mu$. no absorption at 3.0 (—OH) $\mu$.

EXAMPLE 3

8,9-Dihydro-3-Methoxy-5-Methyl-5,8-Methano-5H-Benzocyclohepten-10-One, 10-Ethylene Ketal A mixture of 6,7,8,9-tetrahydro-3-methoxy-5-Methyl-7-p-toluenesulfonyloxy-5,8-methano-5H-benzocyclohepten-10-one, 10-ethylene ketal (132 g.), potassium tert butoxide (100 g.) and 1 liter of dimethyl sulfoxide is heated at 60°–65° under nitrogen and with stirring. The reaction mixture is cooled, diluted with water and extracted with 2 liters of 1:1 diethyl ether: pentane. The organic portion is washed with saturated brine, dried over magnesium sulfate and concentrated to give a yellow oil (68 g.).

I. R. Analysis: No sulfonyl ester absorption at 7.4, 8.6 $\mu$.

NMR Analysis: Signals at $\delta = 5.8$, 2 protons (vinyl proton) ppm.

EXAMPLE 4

8,9-Dihydro-3-Methoxy-5-Methyl-5,8-Methano-5H-Benzocyclohepten-10-One

A solution of 8,9-dihydro-3-methoxy-5-methyl-5,8-methano-5H-benzocyclohepten-10-one, 10-ethylene ketal (68 g.) acetic acid (600 ml.) and water (500 ml.) is refluxed overnight. The solution is concentrated to ~200 ml. and diluted to ~600 ml. with ice water. Crystallization of the product occurs. Filtration gives 52 g. of yellow product with m.p. 80°–105° suitable for use in the next step. Recrystallization of the crude product from ethanol-water gives the title product, m.p. 116°–119° C.

I. R. Analysis: $\lambda_{max}^{KBr}$ 5.65 (<C=O) $\mu$.

EXAMPLE 5

8,9-Dihydro-3-Methoxy-5-Methyl-5,8-Methano-5H-Benzocyclohepten-10-One, Oxime

A mixture of 8,9-dihydro-3-methoxy-5-methyl-5,8-methano-5H-benzocyclohepten-10-one, (52 g.), hydroxyl amine hydrochloride (40 g.), sodium acetate (60 g.), water (100 ml.) and ethanol (1 liter) is refluxed for one-half hour then concentrated. The residue is treated with diethyl ether and water and the organic layer is separated. The organic layer is then washed with dilute sodium bicarbonate, dried over magnesium sulfate and concentrated to give a yellow crystalline product. Recrystallization from isopropanol-water gives 26 g. of the title product, m.p. 150°–156° C. The mother liquors yield additional 13 g., m.p. 130°–145° C., also suitable for further work. Further recrystallization gives an analytical sample with m.p. 154°–156° C.

Analysis for: $C_{14}H_{15}NO_2$. Calculated: C, 73.34; H, 6.59; N, 6.11. Found: C, 73.08; H, 7.03; N, 6.27.

Infrared Analysis: $\lambda_{max}^{KBr}$ 3.0 (—OH) $\mu$ no <C=O absorption at 5.65 $\mu$.

EXAMPLE 6

6,7,8,9-Tetrahydro-3-Methoxy-5-Methyl-5,8-Methano-5H-Benzocyclohepten-10-Amine

A. A mixture of 8,9-dihydro-3-methoxy-5-methyl-5,8-methano-5H-benzocyclohepten-10-one, oxime (12.5 g.), Raney Nickel (No. 28 Grace, 3 teaspoons), ethanol (150 ml.) and concentrated ammonium hydroxide is hydrogenated at 45 psi hydrogen pressure in a Parr shaker apparatus. Hydrogen absorption for two mole equivalents is complete within 1 hour. The catalyst is filtered and the filtrate is concentrated. The concentrated filtrates from three such runs are combined and distilled to give 26.5 g., b.p. 130°–134° at 0.8 mm., of amine product. Gas chromatography of the distillate indicates two amine components of 83% and 17% respectively. The distillate is converted to its hydrogen chloride salt in diethyl ether-ethanol to give 22.5 g. of crystalline salt. Recrystallization of this salt from ethanol-ether gives 20.5 g., m.p. 287°–289°, of 6,7,8,9-tetrahydro-3-methoxy-5α-methyl-5,8- methano-5H-benzocycloheptene-10α-amine, hydrochloride.

Analysis for: $C_{14}H_{20}NOCl$. Calculated: C, 66.26; H, 7.94; N, 5.52. Found: C, 66.03; H, 8.11; N, 5.68.

B. The mother liquors of A above are combined and repeated fractional crystallization from ethanol-ether and finally acetonitrile yields 2.1 g. of essentially pure 6,7,8,9-tetrahydro-3-methoxy-5α-methyl-5,8-methano-5H-benzocyclohepten-10β-amine, hydrochloride, hydrate, m.p. 240°–244°.

Analysis for: $C_{14}H_{20}NOCl \cdot H_2O$. Calculated: C, 61.86; H, 8.16; N, 5.15. Found: C, 62.28; H, 8.50; N, 5.42.

C. A solution of 8,9-dihydro-3-methoxy-5-methyl-5,8-methano-5H-benzocyclohepten-10-amine [1.0 g. of α,β-amine mixture (9:1)] in 100 ml. of ethanol is hydrogenated over 150 mg. of platinum oxide catalyst under 48 psi hydrogen pressure in a Parr apparatus. Uptake of hydrogen is complete in one-half hour. The catalyst is filtered and the filtrate is concentrated. Gas chromatography of the residue identified it as a 9:1 mixture of α/β 6,7,8,9-tetrahydro-3-methoxy-5-methyl-5,8-methano-5H-benzocycloheptene-10-amine.

EXAMPLE 7

8,9-Dihydro-3-Methoxy-5-Methyl-5,8-Methano-5H-Benzocyclohepten-10-Amine

To a stirred slurry of lithium aluminum hydride (3.0 g.) in 100 ml. of ethyl ether under a nitrogen atmosphere is added slowly a solution of aluminum trichloride (10.0 g.) in diethyl ether (100 ml.). The 8,9-dihydro-3-methoxy-5-methyl-5,8-methano-5H-benzocyclohepten-10-one, oxime (5.85 g.) in 50 ml. of diethyl ether is then added slowly to this mixture. The mixture is refluxed for 7 hours and allowed to stand overnight. Concentrated ammonium hydroxide (30 ml.) and isopropanol (50 ml.) are added. The mixture is stirred for one-half hour and filtered. The filter cake is washed with alcohol and the combined filtrate is concentrated. The residue is dissolved in diethyl ether, washed with dilute sodium hydroxide, dried and concentrated to give 4.5 g. of amine product. Gas chromatography shows the amine product to be 9 parts α amine and 1 part β amine. Conversion to its hydrochloride salt in ether-ethanol gives 2.6 g. of 8,9-dihydro-3-methoxy-5α-methyl-5,8-methano-5 H-benzocyclohepten-10α-amine, hydrochloride, m.p. 245°–250°.

Analysis for: $C_{14}H_{18}NOC \cdot \frac{1}{4} H_2O$. Calculated: C, 65.62; H, 7.24; N, 5.47. Found: C, 65.98; H, 7.43; N, 5.18.

EXAMPLE 8

6,7,8,9-Tetrahydro-3-Methoxy-N,5α-Dimethyl-5,8-Methano-5H-Benzocyclohepten-10α-Amine A mixture of 6,7,8,9-tetrahydro-3-methoxy-5α-methyl-5,8-methano-5H-benzocyclohepten-10α-amine, hydrochloride (6.5 g.), ethylchloroformate (8 ml.), methylene chloride (100 ml.) and aqueous sodium bicarbonate (75 ml.) is stirred for 3 hours. The organic layer is separated, washed with dilute acid, dried and concentrated. The residue is added to a stirred mixture of lithium aluminum hydride (4.0 g.) and 200 mg. of tetrahydrofuran. The mixture is refluxed overnight. Concentrated ammonium hydroxide is added and the mixture is filtered. The filtrate is concentrated to give 6.0 g. of product. Conversion to the hydrochloride salt gives salt with m.p. 262°–264° on recrystallization from ethanoldiethyl ether.

Analysis for: $C_{15}H_{22}NOCl$. Calculated: C, 67.27; H, 8.28; N, 5.23. Found: C, 67.09; H, 8.67; N, 5.01.

EXAMPLE 9

6,7,8,9-Tetrahydro-3-Methoxy-N,5α-Dimethyl-5,8-Methano-5H-Benzocyclohepten-10β-Amine In a manner similar to example 8, from 1.3 g. of the hydrochloride salt of 6,7,8,9-tetrahydro-3-methoxy-5α-methyl-5,8-methano-5H-benzocyclohepten-10β-amine there is obtained 1.2 g. of product as the base.

NMR Analysis: Signals at $\delta = 2.48$ (3 protons, N—$CH_3$) ppm.

EXAMPLE 10

6,7,8,9-Tetrahydro-3-Methoxy-N,N,5α-Trimethyl-5,8-Methano-5H-Benzocyclohepten-10α-Amine In a manner analogous to example 8 from 5.0 g. of the product of example 8 there is obtained 4.5 g. of product. Conversion to the hydrochloride salt gives salt with m.p. 257°–258° dec.

Analysis for: $C_{16}H_{24}NOCl$. Calculated: C, 68.19; H, 8.58; N, 4.97. Found: C, 67.79; H, 8.73; N, 4.86.

EXAMPLE 11

6,7,8,9-Tetrahydro-3-Methoxy-N,N,5α-Trimethyl-5,8-Methano-5H-Benzocyclohepten-10β-Amine In a manner analogous to example 8 from 1.2 g. of amine obtained in example 9 there is obtained 1.0 g. of product as the base.

NMR Analysis: Signals at $\delta = 2.33$ (6 protons, $N(CH_3)_2$) ppm.

EXAMPLE 12

8,9-Dihydro-3-Methoxy-N,N,5α-Trimethyl-5,8-Methano-5H-Benzocyclohepten-10α-Amine The amine obtained in example 7 (2.0 g.) is dimethylated in two successive steps in a procedure analogous to example 8 to give 0.55 g. of hydrochloride salt of the title compound with m.p. 253°–255° on recrystallization from ethanol-diethyl ether.

Analysis for: $C_{16}H_{22}NOCl$. Calculated: C, 68.68; H, 7.93; N, 5.01. Found: C, 68.21; H, 8.20; N, 4.70.

EXAMPLE 13

10α-Amino-6,7,8,9-Tetrahydro-5α-Methyl-5,8-Methano-5H-Benzocyclohepten-3-ol

A solution of the α isomer obtained in example 6 (2.5 g.) in 50 ml. of 48% of hydrobromic acid is refluxed for one-half hour under a nitrogen atmosphere. The solution is concentrated and the residue is recrystallized from acetonitrile to give 1.6 g. of the hydrobromide salt of the title product with m.p. 256°–258° C.

Analysis for: $C_{13}H_{18}NOBr$. Calculated: C, 54.94; H, 6.38; N, 4.93. Found: C, 54.64; H, 6.72; N, 5.05.

EXAMPLE 14

10β-Amino-6,7,8,9-Tetrahydro-5α-Methyl-5,8-Methano-5H-Benzocyclohepten-3-ol

In the manner described in example 13, from 0.70 g. of the β isomer obtained in example 6, there is obtained on concentration of the reaction solution, crude hydrobromide salt of the product which is converted to the free base by treatment with concentrated ammonium hydroxide. Recrystallization of the free base from acetonitrile gives 320 mg. of product with m.p. 185°–190°.

Analysis for: $C_{13}H_{17}NO$. Calculated: C, 76.81; H, 8.43; N, 6.89. Found: C, 76.54; H, 8.83; N, 7.29.

EXAMPLE 15

10α-(Dimethylamino)-6,7,8,9-Tetrahydro-5α-Methyl-5,8-Methano-5H-Benzocyclohepten-3-01

In the manner described in example 13, from 3.0 g. of the product of example 10 there is obtained hydrobromide salt of the product which on recrystallization from ethanol-diethyl ether gives 2.3 g. of salt with m.p. 229°–231°.

Analysis for: $C_{15}H_{22}NOBr$. Calculated: C, 57.69; H, 7.10; N, 4.49. Found: C, 57.15; H, 7.36; N, 4.35.

EXAMPLE 16

10β-(Dimethylamino)-6,7,8,9-Tetrahydro-5α-Methyl-5,8-Methano-5H-Benzocyclohepten-3-01

In the manner described in example 13, from 1.0 g. of the product of example II, there is obtained hydrobromide salt of the product which on recrystallization from ethanol-diethyl ether gives 0.800 mg. of salt with m.p. 224°–227°.

Analysis for: $C_{15}H_{22}NOBr$. Calculated: C, 57.69; H, 7.10; N, 4.49. Found: C, 57.54; H, 7.33; N, 4.37.

The subject matter which the applicant regard as their invention is particularly pointed out and distinctly claimed as follows:

1. A process for the preparation of a chemical compound of the formula:

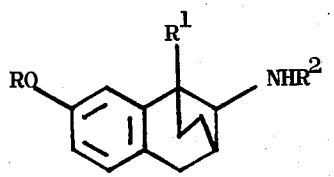

wherein R is lower alkyl, or phen(lower)alkyl; $R^1$ is lower alkyl and $R^2$ is hydrogen, lower alkyl, or phen(lower)alkyl which comprises:
a. treating a compound of the formula:

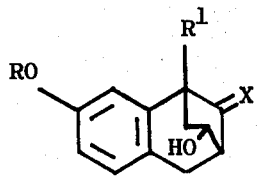

wherein R and $R^1$ are as defined hereinabove; and X is a ketone protecting group from the group ethylene ketal, an ethylene hemithioketal, an ethylene dithioketal, or a semicarbazide; with a compound of the formula:

A—SO₂Y wherein A is halo, and Y is straight or branched chain alkyl of from 1 to 10 carbon atoms, cycloalkyl of from 1 to 10 carbon atoms, or carbocyclic aryl; to produce a compound of the formula:

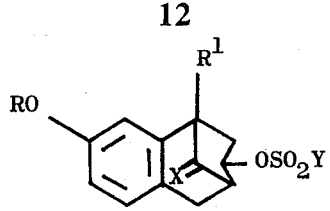

wherein R, $R^1$, X and Y are as defined hereinabove;
b. treating the product of step (a) above with base in the presence of an inert solvent at about 60° to about 65°C. to produce a compound of the formula:

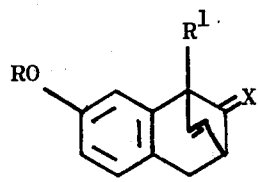

wherein R, $R^1$, and X are as defined hereinabove;
c. removing the protecting group from the ketone function of the product of step (b) to produce a compound of the formula:

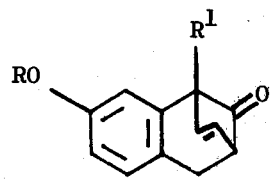

wherein R and $R^1$ are as defined hereinabove;
d. treating the product of step (c) above with a compound of the formula:

H₂N—Z wherein Z is hydrogen, hydroxyl, lower alkyl, or phen(lower)alkyl; to form a compound of the formula:

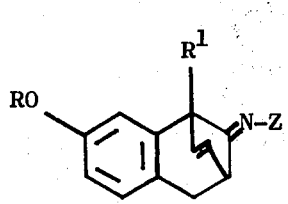

wherein R, $R^1$ and Z are as defined hereinabove; and
e. reducing the imino function and non-aromatic unsaturation of the product of step (d) above by subjecting said product of step d to catalytic hydrogenation, or by reducing said product of step d with a metal hydride reducing agent or with sodium dissolving in alkanol followed by catalytic hydrogenation.

2. A process as described in claim 1 wherein the ketone protecting group is an ethylene ketal.

3. A process as described in claim 1 wherein the ketone protecting group is cleaved by treatment with aqueous acid.

4. A process as described in claim 1 wherein the compound H₂NZ is hydroxylamine.

5. A process as described in claim 1 wherein the reduction of the imino group and the non-aromatic unsaturation is accomplished by catalytic hydrogenation.

6. A process as described in claim 1 wherein the reduction is accomplished by catalytic hydrogenation.

7. A process for the production of compounds of the formula:

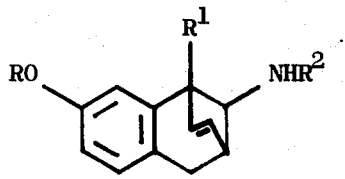

wherein R is lower alkyl, or phen(lower)alkyl; $R^1$ is lower alkyl; and $R^2$ is hydrogen, lower alkyl, lower alkenyl, lower alkynyl, or phen(lower)alkyl; which comprises:

a. treating a compound of the formula:

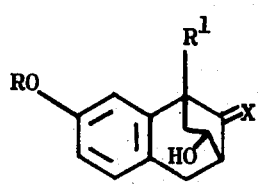

wherein R and $R^1$ are as defined hereinabove; and X is a ketone protecting group from the group ethylene ketal, ethylene hemithioketal, ethylene dithioketal, or semicarbazide; with a compound of the formula:

A—SO$_2$—Y wherein A is halo, and Y is straight or branched chain alkyl of from 1 to 10 carbon atoms, or cycloalkyl of from 1 to 10 carbon atoms, or carbocyclic aryl to produce a compound of the formula:

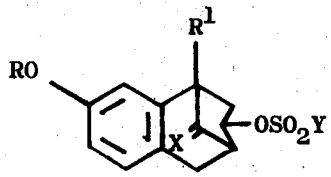

wherein R, $R^1$, X and Y are as defined hereinabove;

b. treating the product of step (a) above with base at about 60° to about 65° C. to produce a compound of the formula:

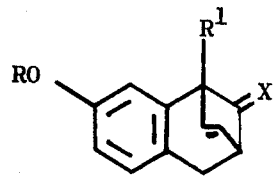

wherein R, $R^1$ and X are as defined hereinabove;

c. removing the protecting group from the ketone function of the product of step (b) to produce a compound of the formula:

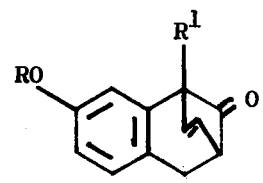

wherein R and $R^1$ are as defined hereinabove;

d. treating the product of step (c) with a compound of the formula:

H$_2$N—Z wherein Z is hydrogen, hydroxyl, lower alkyl, or phen(lower)alkyl; to form a compound of the formula:

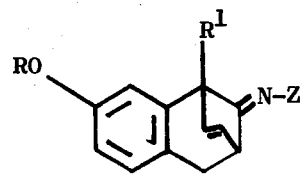

wherein R, $R^1$ and Z are as defined hereinabove; and e. reducing the imino function of the product of step (d) above by reducing said product of step d with a metal hydride reducing agent or with sodium dissolving in an alkanol.

8. A process as described in claim 7 wherein the ketone protecting group is the ethylene ketal.

9. A process as described in claim 7 wherein the ketone protecting group is cleaved by treatment with aqueous acid.

10. A process as described in claim 7 wherein the compound H$_2$NZ is hydroxylamine.

11. A process as described in claim 7 wherein the reduction of the imino group is accomplished by use of a hydride reducing agent.

12. A process as described in claim 7 wherein the hydride reducing agent is lithium aluminum hydride.

* * * * *